United States Patent [19]

Nelson et al.

[11] Patent Number: 4,557,926

[45] Date of Patent: Dec. 10, 1985

[54] METHOD AND TABLET FOR SANITIZING TOILETS

[75] Inventors: G. Douglas Nelson; Steve Vazopolos, both of St. Louis, Mo.

[73] Assignee: Monsanto Company, St. Louis, Mo.

[21] Appl. No.: 742,682

[22] Filed: Jun. 10, 1985

Related U.S. Application Data

[63] Continuation-in-part of Ser. No. 529,830; Sep. 6, 1983.

[51] Int. Cl.$^4$ ............... A61J 3/10; A61K 27/12; C01B 11/02
[52] U.S. Cl. ............... 424/19; 424/22; 424/148; 424/153; 514/241; 514/84
[58] Field of Search ............... 424/44, 145, 153, 19, 424/22, 148; 514/84

[56] References Cited

U.S. PATENT DOCUMENTS

| | | | |
|---|---|---|---|
| 2,540,253 | 2/1951 | Gakenheimer | 424/44 |
| 3,120,378 | 2/1964 | Lee et al. | 424/44 |
| 3,506,756 | 4/1970 | Hoss | 424/44 |
| 3,518,344 | 6/1970 | Welsh et al. | 424/44 |
| 3,518,345 | 6/1970 | Dines et al. | 424/44 |
| 3,692,896 | 9/1972 | Tsumura et al. | 424/44 |
| 3,873,685 | 3/1975 | Kibbel et al. | 424/149 |
| 3,936,385 | 2/1976 | Cheng | 424/44 |
| 4,104,190 | 8/1978 | Hartshorn | 424/149 |
| 4,265,847 | 5/1981 | Hunt et al. | 424/44 |
| 4,389,318 | 6/1983 | Wojtowicz | 424/44 |

FOREIGN PATENT DOCUMENTS

| | | | |
|---|---|---|---|
| 879654 | 8/1971 | Canada | 424/44 |
| 54-44722 | 12/1979 | Japan . | |
| 6904056 | 12/1969 | South Africa . | |
| 1196870 | 7/1970 | United Kingdom . | |
| 1165098 | 7/1971 | United Kingdom . | |
| 1427710 | 3/1976 | United Kingdom . | |

OTHER PUBLICATIONS

Little et al., Tablet Making (2nd Ed.), (1963), Northern Pub. Co., Liverpool, Engl., pp. 47(NACL), 63–65(Lubricants, Boric Acid), 80–88, 112–118, 138(Toilet Tablet), 141–144(Industrial Tablets).

Primary Examiner—Shep K. Rose
Attorney, Agent, or Firm—T. Y. Awalt; J. C. Logomasini; A. H. Cole

[57] ABSTRACT

Disclosed is a tablet for disinfecting flush toilets comprising from about 20% to about 90% alkali metal salt of dichloroisocyanuric acid and at least about 5% of either sodium bromide or potassium bromide. Also disclosed is a method of using the tablet.

8 Claims, No Drawings

METHOD AND TABLET FOR SANITIZING TOILETS

This is a continuation-in-part of our co-pending application Ser. No. 529,830, filed Sept. 6, 1983.

FIELD OF THE INVENTION

This invention relates to sanitizing and disinfecting flush toilets. More particularly, this invention relates to automatic toilet bowl cleaners. This is a continuation in part of our co-pending application Ser. No. 529,830, Filed Sept. 6, 1983.

BACKGROUND

A number of different compositions and methods for disinfecting flush toilets have been proposed. These include various hypochlorite and chloramine compounds, that can be dispensed from a single-compartment dispenser, such as is described in U.S. Pat. No. 4,318,891, or from a two-compartment dispenser such as is described in U.S. Pat. No. 3,618,143 or 4,208,746. The disinfecting composition can be employed as granules, but is more commonly employed as a tablet.

In order to act effectively in automatic toilet bowl cleaners, the disinfectant tablet must have a number of properties. The tablet should have a useful life approaching 300 flushes, and should produce a disinfectant concentration from about 2 to about 30 parts per million, preferably from about 5 to about 120 parts per million, per flush. The tablet must not produce objectionable chloramine or other objectionable odors. The tablets must retain their integrity through the useful life of the toilet bowl cleaner and must not crumble or disintegrate so as to plug the various holes and passages in the dispenser, through which water is circulated as the toilet tank fills and drains. The disinfectant tablet must not cause corrosion of the metal parts of the toilet or other adverse effects on other portions of the fixtures. The tablet must not appreciably contribute to formation of scale or other insolubles or contain insoluble components. Additionally, the tablet must not contribute toxic substances to the sewage system, the water supply, or the environment.

The most commonly used disinfectant tablet materials are calcium hypochlorite and trichloroisocyanuric acid. Each of these substances has major drawbacks. Calcium hypochlorite contains insoluble components that can plug the holes in the dispenser, and also contributes to water hardness and scale formation by adding calcium ions to the water. Trichloroisocyanuric acid is a strong acid and can produce objectionable chloramine odors under some circumstances.

A disinfectant tablet that produces an appropriate concentration of disinfectant, with the requisite lifetime and tablet integrity, and without the negative properties discussed above would be an advancement in the art.

SUMMARY OF THE INVENTION

The invention provides a tablet for disinfecting a flush toilet with from about 20% by weight to about 90% by weight of an alkali metal salt of dichloroisocyanuric acid and at least about 5% by weight of bromine salt selected from the group consisting of sodium bromide and potassium bromide. The preferred alkali metal salts of dichloroisocyanuric acid are sodium and potassium, with sodium being preferred. Particularly preferred is sodium dichloroisocyanuric acid dihydrate. The tablet is essentially free of sodium carbonate/bicarbonate buffer mixture and it is capable of prolonged release of chlorine through metered dispensers when immersed in water. The tablet may, optionally, contain trichloroisocyanuric acid, but, the amount of availale chlorine in the tablet should be less than about 70%, or additional measures must be taken to avoid production of objectionable quantities of chloramine odors. The tablet may also contain one or more mold release agents or other tabletting aids to assist in forming the tablets. The tablet may also contain an inert filler. A particularly preferred embodiment is a tablet with from about 50% by weight to about 75% by weight of sodium dichloroisocyanuric acid dihydrate, from about 5% by weight to about 15% by weight of potassium bromide, from about 10% to about 40% sodium chloride, and from about 1% to about 5% mold release agent or agents. Another particularly preferred embodiment is a tablet with from about 20% by weight to about 52% by weight sodium dichloroisocyanuric acid dihydrate, from about 18% by weight to about 47% by weight potassium bromide, from about 0% by weight to about 60% by weight sodium chloride, and from about 1% by weight to about 5% by weight mold release agent, where the ratio of sodium dichloroisocyanuric acid dihydrate to potassium bromide is substantially stoichiometric. This invention also provides a method for disinfecting a flush toilet by placing a tablet as described above in contact with all or a portion of the water provided to flush the toilet, particularly where the water is contained in a tank that is part of the toilet.

DESCRIPTION OF THE INVENTION

This invention produces the balance of properties for a good toilet bowl disinfectant by combining either sodium or potassium bromide with an alkali metal salt of dichloroisocyanurate, such as sodium dichloroisocyanurate or potassium dichloroisocyanurate. Trichloroisocyanurate can be used as part of this invention, however, the amount of available chlorine in the formulation should be below about 70% to minimize the possibility of generation of objectionable chloramine odors, which can be produced by trichloroisocyanurate. Chloramine odors can also be minimized by other methods, such as addition of an alkaline, preferably above pH 9. Trace levels of chloramine can be acceptable as they are often identified as a "chlorine odor" that is associated with cleanliness, however, high levels of chloramine odor are considered to be very objectionable. This possibility of generation of objectionable chloramine odors represents a serious drawback to use of compositions containing trichloroisocyanurate as the only active ingredient.

Similarly, the use of alkali metal salts of dichloroisocyanurate as the only active ingredient in toilet bowl disinfection applications has serious drawbacks. These salts are substantially more soluble than trichloroisocyanurate, and as a result tablets do not last long enough to be commercially acceptable.

However, the problems associated with use of alkali metal dichloroisocyanurates can be eliminated by addition of sodium bromide, or more preferably, potassium bromide, to the composition. The bromine salt must comprise at least about 5% by weight of the composition, preferably at least about 10%. The bromine salt accomplished this modification in the properties of the composition by a reaction between the alkali metal salt of dichloroisocyanuric acid and the bromide salt to replace some or all of the chlorines by bromines. The properties of the composition continue to improve as the proportion of bromine salt is increased, with optimum properties observed when the bromine salt and alkali metal salt of dichloroisocyanuric acid are present in substantially stoichiometric amounts. The bromide salt can be present in greater than stoichiometric amounts because it also acts as a filler. But, because the bromine salt is more expensive than alternative fillers, there is an economic incentive to use the minimum quantity of the bromine salt that will produce the desired results.

The alkali metal salt of dichloroisocyanurate can be either sodium or potassium dichloroisocyanurate, with sodium being preferred. Most preferred is sodium dichloroisocyanuric acid dihydrate. The alkali metal salt of dichloroisocyanuric acid is used from about 20% to about 90%, or more preferably from about 50% to about 75% by weight of the tablet.

It is also possible to include trichloroisocyanuric acid in the formulation. In order to avoid objectionable chloramine odors, the amount of available chlorine in the tablet should be less than about 70%, or other measures should be taken to avoid generation of chloramine odors. The term "available chlorine" is a commonly used term meaning the amount of active chlorine by weight in the composition, compared with the amount of active chlorine by weight in chlorine gas, expressed as a percent. As used herein "available chlorine" also includes active chlorine that is replace by bromine, since bromine atoms replace chlorine atoms on a one for one basis.

It is also possible for the formulation to include a filler. The filler is an inert substance that can be used to assist in tablettability of the composition, to adjust concentration of the components, to reduce cost, or for other reasons. The filler can be used in any concentration, provided the composition contains the required amount of alkali metal salt of dichloroisocyanuric acid, and provided the composition contains at least about 5% of the bromide salt. The filler is preferably present from about 10% to about 40%. The most common filler is NaCl.

In addition to the components of the formulation described above, the formulation may also contain other ingredients, such as tabletting aids, e.g., mold release agents, binders, etc., corrosion inhibitors, scale inhibitors, and other components known to one skilled in the art. Preferred mold release agents are boric acid and monoglyceryl stearate. It is preferred that one or more mold release agents be present from about 1% to about 5% or more. Tablets are formed in the usual manner.

It is preferred that all of the components of the formulation be fully hydrated, to avoid hydration after tabletting, which can be detrimental to tablet integrity.

The tablet of this invention can either be used alone to provide only disinfection, or can be used as part of a two tablet system to provide more complete cleaning. The second tablet in a two tablet system may contain a detergent, a surfactant, a perfume, a corrosion inhibitor, a scale inhibitor and a dye, and possibly other ingredients. It is preferred that this invention be used as part of a two tablet system.

It is preferred that this invention be used in a dispenser so that the tablet is immersed or partially immersed in water within an enclosure in which the reaction between the bromide salt and the alkali metal salt of dichloroisocyanaurate can occur. Particularly preferred are dispensers similar to those described in U.S. Pat. No. 3,618,143, of U.S. Pat. No. 4,208,747, which are incorporated herein by reference. However, this invention can be used with other dispensers either in the tank or as part of an "under the rim" toilet bowl cleaner.

EXAMPLES 1-6

In each of Examples 1-6, 1.75 inch (3.8 cm.) tablets were prepared in a hydraulic press at 9100-9800 psi (62,700-67,500 kPa) of pressure, using 33 g of each of the following formulations:

Example 1—94% trichloroisocyanurate, 5% sodium bromide. 1% boric acid, and 0.5% monoglyceryl stearate.

Example 2—62% trichloroisocyanurate, 32% potassium dichloroisocyanuric acid, 5% sodium bromide, 1% boric acid, and 0.5% monoglyceryl stearate.

Example 3—30% trichloroisocyanurate, 32% potassium dichloroisocyanuric acid, 32% potassium bromide, 1% boric acid, and 0.5% monoglyceryl stearate.

Example 4—48% sodium dichloroisocyanuric acid dihydrate, 48% sodium chloride, 2% potassium bromide, 1% boric acid, and 0.5% monoglyceryl stearate.

Example 5—56% sodium dichloroisocyanuric acid diydrate, 37% sodium chloride, 5% potassium bromide, 1% boric acid, and 0.5% monoglyceryl stearate.

Example 6—64% sodium dichloroisocyanuric acid dihydrate, 32% sodium chloride, 2% potassium bromide, 1% boric acid, and 0.5 monoglyceryl stearate.

All of the compositions formed good tablets. Each of the tablets was placed in a dispenser similar to that described in U.S. Pat. No. 4,208,747. The dispenser was placed in a container of water and periodically was raised out of the water to similate flushing action in a toilet.

The amount of disinfecting halogen (chlorine and bromine) was determined amperometri-cally. From these data, the concentration of halogen (expressed as parts per million chlorine) dispensed to an average toilet was estimated. This procedure was repeated for each of the Examples so that the lifetime of each of the tablets could be estimated. The results, along with the available chlorine for each of the formulations are included in Table I.

TABLE I

| Ex. Tablet No. | % Available Chlorine | Halogen Concentration Range in Toilet (ppm) (Chlorine) | Estimated Life (Days) |
| --- | --- | --- | --- |
| 1 | 84.2 | 1.4–5 | 30+ |
| 2 | 74.4 | 2.0–4 | 30+ |
| 3 | 42.9 | 0.8–4 | 30 |
| 4 | 26.8 | 4.2–12 | 4 |
| 5 | 31.0 | 2.0–8 | 30 |
| 6 | 35.8 | 8.0–15 | 7 |

Examples 1 and 2 both produced objectionable chloramine odor. Each of the tablets maintained its integrity throughout the test with no problems with clogging of the passage in the dispenser. Each oF Examples 4 and 6, which contained only 2% potassium bromide resulted in very short lifetimes, showing the solubility of the sodium dichloroisocyanuric acid dihydrate. Example 5, with 5% potassium bromide showed a marked increase in lifetime, demonstrating the remarkable effect of this invention. Both Examples 3 and 5, within the scope of this invention produced very good results with adequate disinfectant concentration, good lifetime, good tablet integrity, and no objectionable chloramine odor.

EXAMPLES 7-10

In Examples 7-10, 50 g tablets of similar diameter to those of Examples 1-6 were prepared in a similar manner, using the following formulations:

Example 7—56% sodium dichloroisocyanuric acid dihydrate, 37% sodium chloride, 5% potassium bromide, 1% boric acid, and 1% monoglyceryl stearate.

Example 8—61% sodium dichloroisocyanuric acid dihydrate, 30% sodium chloride, 5% potassium bromide, 1% boric acid, and 1% monoglyceryl stearate.

Example 9—51% sodium dichloroisocyanuric acid dihydrate, 47% potassium bromide, 1% boric acid, and 1% monoglyceryl stearate.

Example 10—73% sodium dichloroisocyanuric acid dihydrate, 10% sodium chloride, 15% potassium bromide, 1% boric acid, and 1% monoglyceryl stearate.

In Example 9, the amount of potassium bromide is approximately the stoichiometric amount required to convert all of the sodium dichloroisocyanuric acid to potassium dibromoisocyanuric acid. Each of the tablets was placed in a dispenser similar to that sued in Examples 1-6 and placed in the tank of a standard flush toilet that was rigged to flush approximately hourly. Water samples were taken periodically and analyzed as in Examples 1-6, and tablet life was determined. The results ware reported in Table II.

TABLE II

| Example Number | Halogen Concentration Range (ppm Chlorine) | Tablet Life (Flushes) |
|---|---|---|
| 7 | 2-8 | >300 |
| 8 | 2-3 | 291 |
| 9 | 2-3 | 443 |
| 10 | 2-3 | 363 |

Each of Examples 7—10 performed well and did not clog the passages in the dispenser. Assuming approximately 10 flushes per day, each of the tablets would be expected to last about 30 days or more.

In addition to altering the composition of the tablets, it is also possible to fine tune the performance of a tablet by altering its size or shape, or by altering the tabletting pressure, or other tabletting changes known to one skilled in the art.

One skilled in the art will understand and appreciate that various changes or alternations can be made in the Examples above, without departing from the spirit or scope of this invention.

We claim:

1. A tablet suitable for disinfecting flush toilets comprising from about 20% by weight to about 90% weight of an alkali metal salt of dichloroisocyanuric acid and at least 5% by weight of bromine salt selected from the group consisting of sodium bromide and potassium bromide, said tablet being essentially free of sodiun carbonate/bicarbonate buffer mixtures, and capable of prolonged release of chlorine through metered dispensers when immersed in water.

2. A tablet of claim 1, further comprising a mold release agent.

3. A tablet of claim 1, further comprising trichloroisocyanuric acid.

4. A tablet of claim 1 further comprising an inert filler.

5. A tablet of claim 1 in which the alkali metal salt of dichloroisocyanuric acid is sodium dichloroisocyanuric acid dihydrate.

6. A tablet of claim 1 in which the bromine salt is potassium bromide.

7. A tablet suitable for disinfecting a flush toilet, comprising from about 20% by weight to about 52% by weight sodium dichloroisocyanuric acid dihydrate, from about 18% by weight to about 47% by weight potassium bromide, from about 0°% by weight to about 60by weight sodium chloride, and from about 1% by weight to about 5% by weight mold release agent, in which the ratio of sodium dichloroisocyanuric acid dihydrate to potassium bromide is substantially stoichiometric. Said tablet being essentially free of sodium carbonate/bicabonate buffer mixtures and capable of prolonged release of chlorine through metered dispensers when immersed in water.

8. A tablet suitable for disinfecting a flush toilet comprising from about 50% by weight to about 75% by weight of sodium dichloroisocyanuric acid dihydrate, from about 5% by weight to about 15% by weight of potassium bromide, from about 10% by weight to about 40% by weight sodium chloride and from about 1% to about 5% mold release agent, in which the ratio of sodium dichloroisocyanuric acid dihydrate to potassium bromide is substantially stoichiometric, said tablet being essentially free of sodium carbonate/bicarbonate buffer mixtures and capable of prolonged release of chlorine through metered dispensers when immersed in water.

* * * * *

UNITED STATES PATENT AND TRADEMARK OFFICE
CERTIFICATE OF CORRECTION

PATENT NO. : 4,557,926
DATED : 12/10/85
INVENTOR(S) : G. Douglas Nelson, et al

It is certified that error appears in the above—identified patent and that said Letters Patent is hereby corrected as shown below:

Column 1, line 30, delete "120" and insert therefor --20--.

Column 4, line 4, delete "of" and insert therefor --or--.

Column 5, line 30, delete "ware" and insert therefor --are--.

Column 6, line 28, delete "0°%" and insert therefor --0%--.

Column 6, line 29, delete "60by" and insert therefor --60%--.

Signed and Sealed this

Eighth Day of July 1986

[SEAL]

Attest:

DONALD J. QUIGG

Attesting Officer

Commissioner of Patents and Trademarks